US005092890A

United States Patent [19]

Pohlemann et al.

[11] Patent Number: 5,092,890

[45] Date of Patent: Mar. 3, 1992

[54] IMPLANT MATERIALS FOR HARD TISSUE

[75] Inventors: Heinz Pohlemann; Bernd Hisgen, both of Limburgerhof, Fed. Rep. of Germany

[73] Assignee: BASF Aktiengesellschaft, Ludwigshafen, Fed. Rep. of Germany

[21] Appl. No.: 459,347

[22] Filed: Dec. 29, 1989

[30] Foreign Application Priority Data

Jan. 12, 1989 [DE] Fed. Rep. of Germany ....... 3900708

[51] Int. Cl.[5] .................................... A61F 2/28

[52] U.S. Cl. .................................... 623/1 G

[58] Field of Search .................................... 623/16

[56] References Cited

U.S. PATENT DOCUMENTS

| | | | |
|---|---|---|---|
| 4,097,935 | 7/1978 | Jarcho | 623/16 |
| 4,118,372 | 10/1978 | Schaefgen | 528/190 |
| 4,131,597 | 12/1978 | Bluethgen et al. | 623/16 |
| 4,222,128 | 8/1980 | Tomonaga et al. | |
| 4,567,227 | 1/1986 | Kiss | 524/538 |
| 4,645,503 | 2/1987 | Lin et al. | 623/16 |
| 4,722,948 | 2/1988 | Sanderson | 523/115 |
| 4,843,112 | 6/1989 | Gerhart et al. | 623/16 X |
| 4,889,911 | 12/1989 | Pielartzik et al. | 528/182 |

FOREIGN PATENT DOCUMENTS

| | | |
|---|---|---|
| 0192068 | 8/1986 | European Pat. Off. . |
| 2821354 | 5/1977 | Fed. Rep. of Germany . |
| 3542535 | 7/1986 | Fed. Rep. of Germany . |
| 2169914 | 11/1975 | United Kingdom . |
| 0050215 | 4/1982 | United Kingdom . |
| 8201310 | 7/1983 | World Int. Prop. O. . |

*Primary Examiner*—Randall L. Green
*Assistant Examiner*—Paul Prebilic
*Attorney, Agent, or Firm*—Oblon, Spivak, McClelland, Maier & Neustadt

[57] ABSTRACT

An implant material for replacing hard tissue containing as essential components A) 30 to 95% by weight of a thermotropically mesomorphic polymer, B) 5 to 70% by weight of an apatite and C) 0 to 60% by weight of a fibrous or particulate filler which differs from B).

11 Claims, No Drawings

IMPLANT MATERIALS FOR HARD TISSUE

The present invention relates to an implant material for replacing hard tissue in the body, containing as essential components A) 30 to 95% by weight of a thermotropically mesomorphic polymer, B) 5 to 70% by weight of an apatite and C) 0 to 60% by weight of fibrous or particulate fillers which differ from B), or mixtures thereof.

Surgical or orthopedic treatments which result in a loss of pieces of bone or of joints frequently have to be followed by prosthetic operations in order to replace the pieces which have been removed.

The main constituents of bone in human and animal bodies are collagen (organic material) and apatite (inorganic material).

Implant materials which have hitherto been employed to replace hard tissue are natural materials, metallic or ceramic materials and—recently—systems based on reinforced thermoplastic polymers.

Although natural materials such as ivory or animal bone are often satisfactorily compatible with the tissue into which they are implanted, nevertheless their mechanical properties are difficult to predict and poorly reproducible.

The compatibility of metallic, ceramic or polymeric materials with biological materials is often low, which may result in inflammations and infections on insertion of the prosthesis in particular.

Also known are implant materials composed of a combination of metallic or ceramic materials and polymers, the latter being intended, in particular, to seal the material surface, which leads to a low coefficient of friction. The fixing to the bone is often brought about by in situ polymerization which, because of the local heating which occurs during this, may lead to serious inflammations and tissue damage.

Because, as already mentioned, bone essentially consists of collagen and apatite, there has been no lack of attempts to develop implant materials which contain these materials.

Sintered apatites have attracted interest as replacements for bone and teeth, because of their compatibility with biological tissue, but the great brittleness and the inadequate mechanical strength hinder their wide use (cf. H. Aoki et al., Ceramics 10 (1975) 57-66).

DE-A 2,821,354 decribes composite implant materials comprising a ceramic body as continuous phase with perforations filled with synthetic resin, and, although these have certain advantages over sintered apatites with regard to mechanical properties, they are not yet completely satisfactory. In addition, the process of manufacture of products which contain sintered apatite is relatively costly.

WO 82/01310 describes a composite material which consists of a homo- or copolyolefin with a weight average molecular weight of more than 20,000 and up to 80% by weight of a particulate inorganic filler. The preferred example mentioned for the inorganic filler is natural or synthetic hydroxyapatite.

Although materials of this type have satisfactorily reproducible mechanical properties, nevertheless their strength and rigidity, in particular, still require improvement.

DE-A 3,542,535 also relates to implant materials for replacing hard tissue in the live body. These consist of 10 to 90% by weight of glass fibers which consist predominantly of calcium phosphate, and 10 to 90% by weight of organic polymers, particularly preferred being polyethylene, polypropylene, poly(methyl methacrylate) and poly(trifluoroethyl methacrylate); the two latter polymers are said to result in particularly high strengths, but these are still not yet completely satisfactory.

Hence the object of the present invention was to make available implant materials for replacing hard tissue in the body, which are satisfactorily compatible with biological tissue and whose mechanical properties are satisfactorily reproducible. It was particularly intended to improve the rigidity and strength by comparison with known polymer-based materials.

This object is achieved according to the invention by the implant materials defined in the introduction.

The implant materials according to the invention contain as component A) 30 to 95, preferably 35 to 90, and in particular 40 to 75, % by weight of a thermotropically mesomorphic polymer. The latter have been described in recent years in a large number of publications and patent applications.

Thermotropically mesomorphic polymers have an anisotropic melt phase which is easy to detect using the polarizing microscope method described in U.S. Pat. No. 4,118,372. Between crossed polarizers, the polymer melts, which are applied in a layer thickness of 10 μm between glass plates, have textures which can be assigned to a mesomorphic phase.

To achieve an anisotropic (liquid crystalline) melt phase it is usually necessary for the main chain to have a certain degree of linearity which can be achieved by appropriate choice of the ratios of monomer amounts. The anisotropy of the melt phase, and the orientation of the polymer molecules associated therewith, result in very high strengths and rigidities in shaped articles produced from polymers of this type.

It should be emphasized that, in principle, all thermotropically mesomorphic polymers, irrespective of the composition, are suitable as component A) for producing the implant materials according to the invention.

It is possible to say in general that thermotropically mesomorphic polymers contain units which are derived from $a_1$) aromatic or aliphatic dicarboxylic acids, $a_2$) aromatic or aliphatic diols, diamines or corresponding monomers with an amino and a hydroxyl group, $a_3$) aromatic hydroxy and amino carboxylic acids and $a_4$) aromatic thiocarboxylic acids and dithiols or thiophenols.

It is possible to prepare from these monomers, by appropriate combination, for example polyesters, polyester amides, polyester imides, polyester carbonates, polyether esters, polyether ester amides, polyester amide imides, polyester carbamides and polyether ester imides.

The composition of these products can vary within wide limits, and a large number of monomers can be employed. It is essential that the polymers have thermotropically mesomorphic properties, which can easily be checked by the method which has already been mentioned and is described in U.S. Pat. No. 4,118,372.

Not all combinations of monomers $a_1$) to $a_4$) in any desired molar ratio result in thermotropically mesomorphic polymers, and it is scarcely possible to make a general statement about suitable ratios of amounts.

However, the relevant literature and a large number of patent applications describe suitable thermotropically mesomorphic systems which will now be illustrated in detail below, firstly by a list of suitable examples of monomers and corresponding polymers. Monomers $a_1$: Terephthalic acid, isophthalic acid, 2,6-naphthalenedicarboxylic acid, 2,7-naphthalenedicarboxylic acid, 4,4,'-dicarboxydiphenyl, 4,4''-dicarboxyterphenyl, dicarboxydiphenyl derivatives of the general formulae I and II

| | | |
|---|---|---|
| 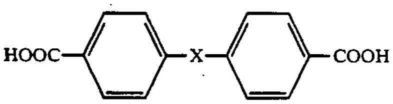 | $X = O$ | 4,4'-dicarboxydiphenyl ether |
| | $X = CH_2CH_2$ | 1,2-di(4-carboxyphenyl)ethane |
| | $X = OCH_2CH_2O$ | 1,2-di(4-carboxyphenoxy)ethane |
| | $X = O(CH_2)_4O$ | 1,4-di(4-carboxyphenoxy)butane |
| (I) | | |
| 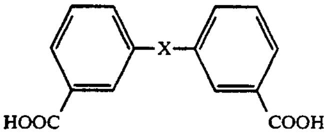 | $X = O$ | 3,3'-dicarboxydiphenyl ether |
| | $X = CH_2CH_2$ | 1,2-di(3-carboxyphenyl)ethane |
| | $X = OCH_2CH_2O$ | 1,2-di(3-carboxyphenoxy)ethane |
| | $X = O(CH_2)_4O$ | 1,4-di(3-carboxyphenoxy)butane |
| (II) | | |
| 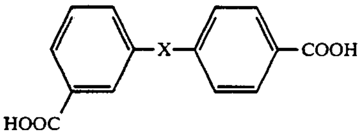 | $X = O$ | 3,4'-dicarboxydiphenyl ether |
| | $X = CH_2CH_2$ | 1,2-(3,4'-dicarboxydiphenyl)ethane |
| | $X = OCH_2CH_2O$ | 1,2-(3,4'-dicarboxydiphenoxy)ethane |
| | $X = O(CH_2)_4O$ | 1,4-(3,4'-dicarboxydiphenoxy)butane |

Dicarboxylic acids of the general formula III and IV should also be mentioned

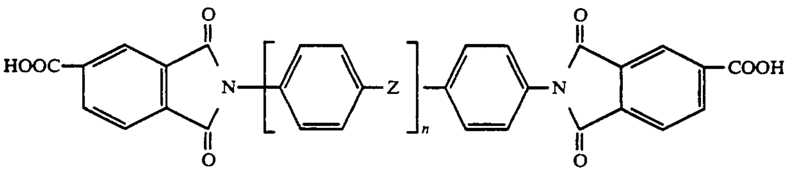

(III)

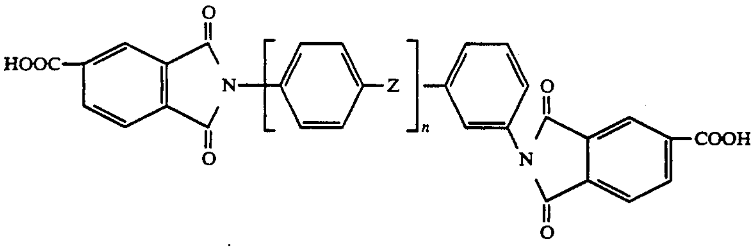

(IV)

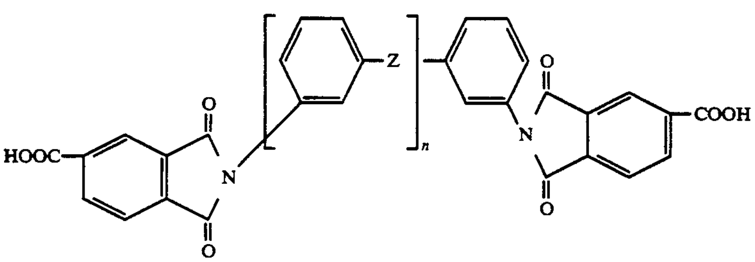

(V)

where Z is —O—, —S—, —$SO_2$—, —$CH_2$—, —$C(CH_3)_2$ or a chemical bond and n is 0 or 1.

Examples of these are

| | |
|---|---|
| $Z = O$ | 4,4'-, 3,4'- and 3,3'-di(4-carboxy-N-phthalimido)diphenyl ether |
| $Z = CH_2$ | 4,4'-, 3,4'- and 3,3'-di(4-carboxy-N-phthalimido)diphenylmethane |
| $Z = SO_2$ | 4,4'-, 3,4'- and 3,3'-di(4-carboxy-N-phthalimido)diphenyl sulfone |
| $Z = CO$ | 4,4'-, 3,4'- and 3,3'-di-(4-carboxy-N-phthalimido)diphenyl ketone |
| $Z = S$ | 4,4'-, 3,4'- and 3,3'-di-(4-carboxy-N-phthalimido)diphenyl sulfide |

and, for example,

| | |
|---|---|
| $Z = C(CH_3)_2$ | 2,2-di[4,4'-di(4-carboxy-N-phthalimido)-diphenyl]propane. |

Likewise suitable are p,p'-, m,m'-, and p,m'- dicarboxydiphenyl carbonates of the general formulae VI to VIII

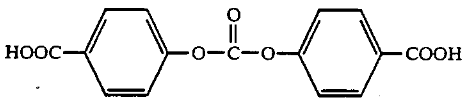
(VI)

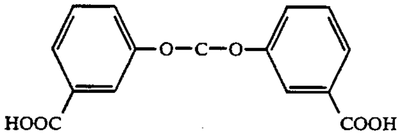
(VII)

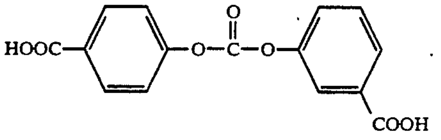
(VIII)

The abovementioned carboxylic acids can also have substituents such as C-–$C_4$-alkyl, $C_1$–$C_4$-alkoxy or halogen. Finally, mention should also be made of some aliphatic dicarboxylic acids such as cis- and trans-1,4-cyclohexanedicarboxylic acid and 1,3-cyclohexanedicarboxylic acid as well as the appropriately substituted derivatives thereof.

Monomers $a_2$: Hydroquinone, methylhydroquinone, phenylhydroquinone, tert.-butylhydroquinone, chlorohydroquinone, 4,4'-dihydroxydiphenyl, 1,4-di(4-hydroxyphenyl)benzene, 1,2-di(4-hydroxyphenoxy)ethane, 4,4'-dihydroxydiphenyl ether, 4,4'-dihydroxydiphenyl sulfone, 3,3'-dihydroxydiphenyl, 3,3'-dihydroxydiphenyl ether, 3,4'-dihydroxydiphenyl, 3,4'-dihydroxydiphenyl ether, 2,2-di(4-hydroxyphenyl)propane, 1,6', 2,6' and 2,7-dihydroxynaphthalene, 3,3',5,5'-tetramethyl-4,4'-dihydroxydiphenyl, 4,4'-di(phydroxyphenoxy)diphenyl sulfone, urea, 1,4-diaminobenzene, 1,3-diaminobenzene, 3-aminophenol, 4-aminophenol, trans- and cis-1,4-cyclohexanediol, trans-1,3-cyclohexanediol and cis-1,2-cyclohexanediol. It is obvious that once again in general substituents can be present as in the monomers $a_1$.

Monomers $a_3$: 4-Hydroxyben-zoic acid, 3-hydroxybenzoic acid, 6-hydroxynaphthalene-2-carboxylic acid, 6-hydroxynaphthalene-1-acid, 3-aminobenzoic acid, 4-aminobenzoic acid and the $C_1$–$C_4$-alkyl, $C_1$–$C_4$-alkoxy or halogen derivatives thereof such as 3-methyl-4-hyiroxybenzoic acid, 3,5-dimethyl-4-hydroxybenzoic acid, 2,6-dimethyl-4-hydroxybenzoic acid, 3-methoxy-4-hydroxybenzoic acid and 2,5-dichloro-4-hyiroxybenzoic acid, to mention just a few examples.

Monomers $a_4$: 4-Mercaptobenzoic acid, 3-mercaptobenzoic acid, 6-mercaptonaphthalene-2-carboxylic acid, 2,7-dimercaptonaphthalene, 2,6-dimercaptonaphthalene, 1,4-dimercaptobenzene and 1,3-dimercaptobenzene as well as the $C_1$–$C_4$-alkyl, $C_1$–$C_4$-alkoxy and halogen derivatives thereof.

Further suitable monomers from groups $a_1$) to $a_4$) are listed, for example, in EP-A 206,600.

A number of preferred thermotropically mesomorphic polymers are presented hereinafter.

1. Thermotropically mesomorphic polyesters composed of 1a) 10 to 25 mol-% of repeating units of the formula

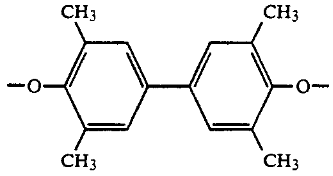

3,3',5,5'-tetramethyl-4,4,'-dihydroxydiphenyl is advantageously used as starting material;

1b) 5 to 15 mol-% of repeating units of the formula

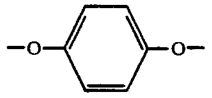

hydroquinone is used as preferred starting material;

1c) 5 to 15 mol-% of repeating units of the formula

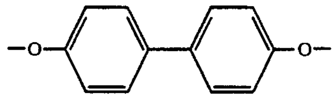

4,4'-dihydroxydi-phenyl is used, for example, as starting compound;

1d) at least 10 mol-% of repeating units of the formula

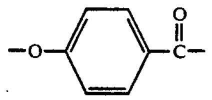

4-hydroxybenzoic acid is used as preferred starting compound;

1e) a molar amount which is equivalent to the total of 1a), 1b) and 1c) of repeating units of the formula

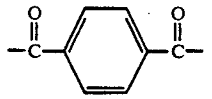

terephthalic acid is used, for example, as suitable starting compound.

In preferred completely aromatic polyesters of this type, some of the units b) and/or c) are replaced by 1f) repeating units of the formula

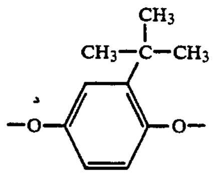

a suitable starting material for this is, for example, tert.-butylhydroquinone and/or 1g) repeating units of the formula

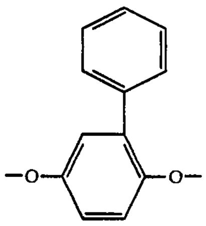

phenylhydroquinone is used as preferred starting compound.

Completely aromatic polyesters of this type advantageously contain the repeating units 1f) and/or 1g) in an amount of from 2 to 20 mol-%. It has furthermore proved advantageous for the total of the molar proportions of units 1a) and 1f) and/or 1g) to be from 20 to 40 mol-%.

In other preferred completely aromatic polyesters, some of the units 1b) and/or 1c) are replaced by 1h) repeating units of the formula

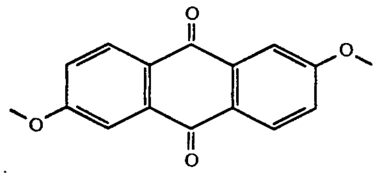

1i) repeating units of the formula

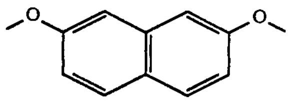

1j) repeating units of the formula

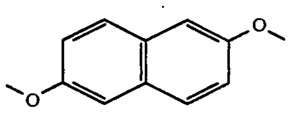

and/or
1k) repeating units of the formula

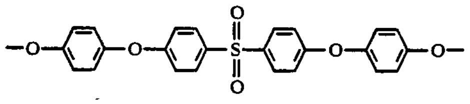

Used as starting material for component 1h) is 2,6-dihydroxyanthraquinone, for component 1i) is 2,7-dihydroxynaphthalene, for component 1j) is 2,6-dihydroxynaphthalene and for component 1k) is 4,4,'-di(p-hydroxyphenoxy)diphenyl sulfone.

It has proven appropriate for the total of the molar proportions of the units 1a), 2h), 1i), 1j) and 1k) in the polyesters according to the invention to be from 20 to 40 mol-%.

It is advantageous to use in each case the amount of terephthalic acid equivalent to the total of the dihydroxy compounds.

Polyesters of this type are described in EP-A 226,839.

2. Thermotropically mesomorphic polyesters composed of 2a) 5 to 35 mol-% of repeating units of the formula

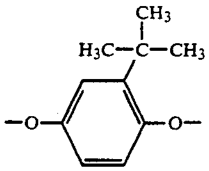

t-butylhydroquinone is used as starting compound;

2b) 3 to 15 mol-% of repeating units of the formula

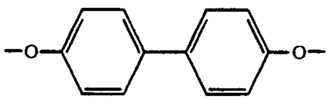

4,4,'-dihydroxybiphenyl is used as starting compound;

2c) a molar amount equivalent to the total of 2a) and 2b) of repeating units of the formula

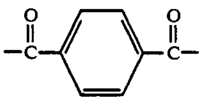

terephthalic acid is used as starting compound;

2d) at least 10 mol-% of repeating units of the formula

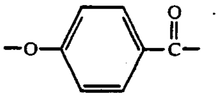

p-hydroxybenzoic acid is used as starting compound.

In preferred polyesters of this type, some of the units b) are replaced by 2e) repeating units of the formula

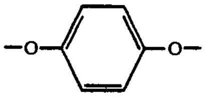

(a suitable starting compound is hydroquinone) and/or 2f) repeating units of the formula

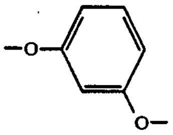

(a suitable starting compound is resorcinol) and/or 2g) repeating units of the formula

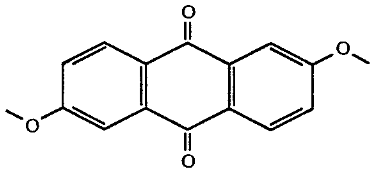

(a suitable starting compound is 2,6-dihydroxyanthraquinone) and/or 2h) repeating units of the formula

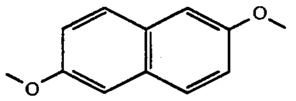

2,6-dihydroxyna-phthalene is used as suitable starting compound.

Polyesters of this type contain the units 2e), 2f) and/or 2g) in an amount of from 5 to 12 mol-%. It has furthermore proven advantageous for the molar proportion of units 2a) to be from 15 to 25 mol-%. In particularly advantageous polyesters the molar proportion of the total of 2a) and one or more units 2e), 2f) and 2g) is from 25 to 35 mol-%.

It has proven advantageous for some of the units 2c to be replaced by units of the formula

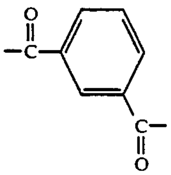

Isophthalic acid is used as suitable starting compound.

It is obvious that it is advantageous in each case to use the amount of terephthalic acid and/or isophthalic acid which is equivalent to the total of the hydroxy compounds.

Polyesters of type 2 are described in EP-A 226,078.

3. Thermotropically mesomorphic polyether esters composed of 3a) at least 10 mol-% of repeating units of the formula

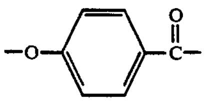

p-hydroxybenzoic acid is used, for example, as starting material, 3b) a molar amount equivalent to the total of c) and d) of repeating units of the formula

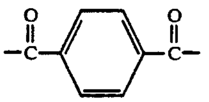

where terephthalic acid is used as preferred starting compound, 3c) 5 to 20 mol-% of repeating units of the formula

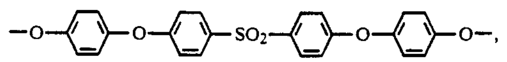

4,4,'-di(p-hydroxyphenoxy)diphenyl sulfone is used, for example, as starting compound, and 3d) 10 to 30 mol-% of repeating units of the formula

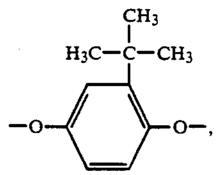

tert.-butylhydroquinone is advantageously used as starting compound.

Preferred polyether esters of this type contain, besides component 3a), 10 to 15 mol-% of component 3c), 15 to 25 mol-% of component 3d) and a molar amount equivalent to the total of 3c) and 3d) of component 3b).

Some of the units 3d) can be replaced by 3e) repeating units of the formula

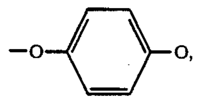

hydroquinone is used, for example, as starting compound, and/or 3f) repeating units of the formula

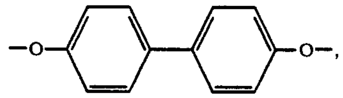

4,4,'-dihydroxydiphenyl is preferably used as a suitable starting compound, and/or 3g) repeating units of the formula

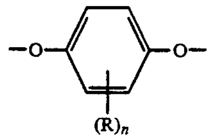

where R is methyl, phenyl or chlorine, and n is 1, 2 or 3.

Suitable starting compounds are methylhydroquinone, trimethylhydroquinone, phenylhydroquinone and chlorohydroquinone.

It is advantageous for completely aromatic polyether esters of this type to contain the repeating units 3e) and/or 3f) in an amount of from 5 to 10 mol-%. In another preferred composition, the completely aromatic polyether esters contain the component 3g) in an amount of from 5 to 20 mol-%.

Products of this type are the subject-matter of EP-A 225,539.

4. Polyester carbamides composed of 4a) at least 20 mol-% of repeating units of the formula

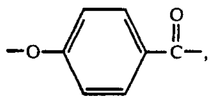

p-hydroxybenzoic acid is, for example, a suitable starting compound;

4b) 5 to 15 mol-% of repeating units of the formula

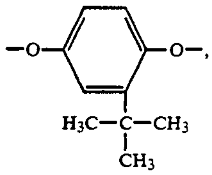

an example of a suitable starting compound is t-butylhydroquinone;

4c) 5 to 15 mol-% of repeating units of the formula

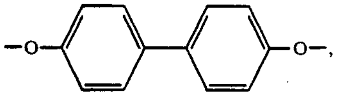

a suitable starting compound is, for example, 4,4'-dihydroxydiphenyl;

4d) 1 to 10 mol-% of repeating units of the formula

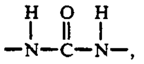

a preferred starting compound is urea;

4e) a molar amount equivalent to the total of 4b), 4c) and 4d) of repeating units of the formula

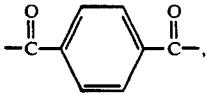

an example of a suitable starting compound is terephthalic acid.

Some of the repeating units 4b) can be replaced by 4f) repeating units of the formula

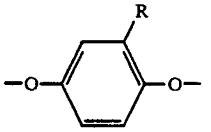

where R is $C_1$–$C_4$-alkyl, except tert.-butyl, halogen or phenyl which can contain methyl substituents.

Examples of suitable starting compounds are methylhydroquinone, ethylhydroquinone, isopropylhydroquinone, chlorohydroquinone or phenylhydroquinone.

The content of repeating units 4f) is advantageously from 2 to 10 mol-%.

It has furthermore proven advantageous for the molar proportion of the total of components 4b) and 4d) in the polyester carbamides to be from 15 to 20 mol-%.

In other polyester carbamides some of the component 4c) is replaced by at least one of the repeating units of the formulae

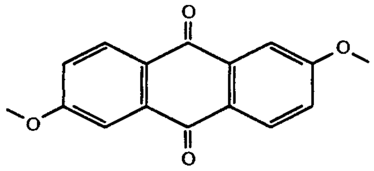

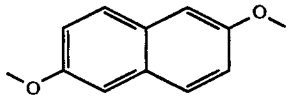

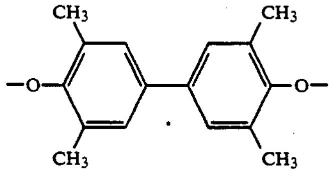

Suitable starting compounds for the repeating units of these formulae are 2,6-dihydroxyanthraquinone, 2,6-dihydroxynaphthalene and 3,3',5,5'-tetramethyl-4,4'-dihydroxybiphenyl. The proportion of the repeating units of these formulae advantageously totals from 2 to 10 mol-%.

Products of this type are described in EP-A 230,551.

5. Polyesters composed of 5a) at least 10 mol-% of repeating units of the formula

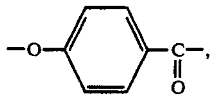

where 4-hydroxybenzoic acid is used as starting compound; 5b) a molar amount equivalent to the total of components 5c) and 5d) of repeating units of the formula

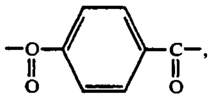

terephthalic acid is advantageously used as starting compound;

5c) 3 to 20 mol-% of repeating units of the formulae

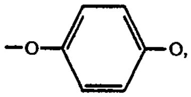

hydroquinone is used, for example, as starting compound;

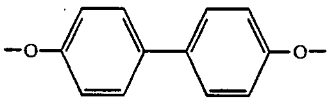

4,4'-dihydroxybiphenyl is used, for example, as starting compound;

5d) 5 to 30 mol-% of repeating units of the formula

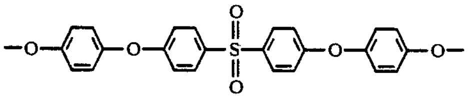

where 4,4'-di(p-hydroxyphenoxy)diphenyl sulfone is advantageously used as starting compound.

Preferred polyether esters are composed of at least 20 mol-%, advantageously up to 50 mol-%, of component 5a), 10 to 25 mol-% of component 5d), 5 to 15 mol-% of component 5c) and a molar amount equivalent to the total of 5c) and 5d) of component 5b). The polyether esters advantageously contain as component 5c) from 5 to 15 mol-% of repeating units which are derived from hydroquinone or a mixture of hydroquinone and dihydroxydiphenyl.

Polyether esters of the abovementioned type are described in EP-A 226,847.

6. Polyester amides composed of 6a) 5 to 35 mol-% of repeating units of the formula

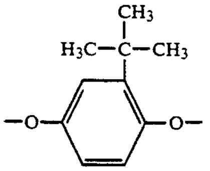

6b) 5 to 15 mol-% of repeating units of the formula

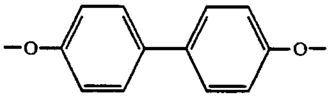

6c) a molar amount equivalent to the total of components 6a) and 6b) and, where appropriate, 6e) of repeating units of the formula

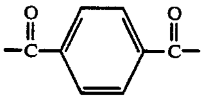

6d) at least 10 mol-% of repeating units of the formula

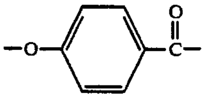

6e) 2 to 15 mol-% of repeating units of the formulae

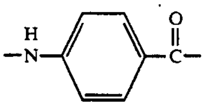

or

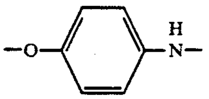

where some of the repeating units of the last formula can be replaced by repeating units of the formula

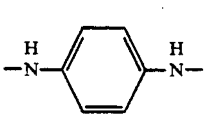

with the proviso that the total of the molar proportions of components 6a), 6b), 6c), 6d) and 6e) is 100 mol-% in each case.

The repeating units 6a) to 6e) are preferably derived from the following starting compounds:

6a) t-butylhydroquinone 6b) 4,4'-dihydroxydiphenyl 6c) terephthalic acid 6d) p-hydroxybenzoic acid 6e) p-aminobenzoic acid, p-aminophenol and 1,4-diaminobenzene.

Polyester amides with these structural units are described in EP-A 230,545.

7. Polyester amides composed of 7a) 3 to 30 mol-% of repeating units of the formula

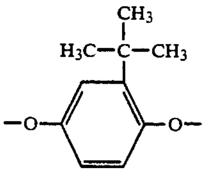

7b) 3 to 30 mol-% of repeating units of the formulae

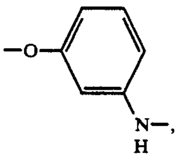

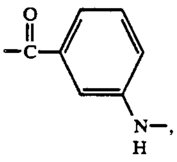

7c) 2 to 25 mol-% of at least one of the repeating units of the formulae

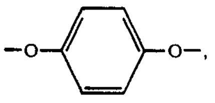

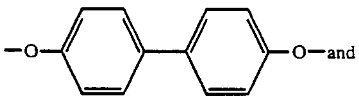
and

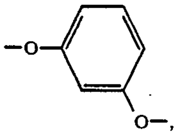

7d) a molar amount equivalent to the total of components 7a), 7b) and 7c), except the second repeating units of the formula 7b), of repeating units of the formula

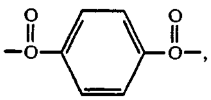

where some of these repeating units can be replaced by those of the formula

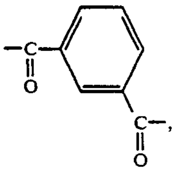

7e) where appropriate 5 to 25 mol-% of repeating units of the formula

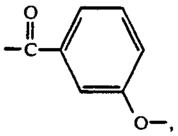

7f) repeating units of the formula

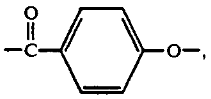

where the molar proportions of components 7a) to 7f) total 100 mol-% in each case.

The units 7a) to 7f) are preferably derived from

7a): t-butylhydroquinone

7b): m-aminophenol or m-aminobenzoic acid,

7c): hydroquinone, 4,4'-dihydroxydiphenyl or resorcinol,

7d): terephthalic acid or isophthalic acid

7e): m-hydroxybenzoic acid and

7f): p-hydroxybenzoic acid.

Preferred polyester amides contain 5 to 20 mol-% of repeating units 7a), 5 to 20 mol-% of repeating units of the formula 7b), which are derived from m-aminophenol, and 5 to 20 mol-% of the formula 7c), in particular those units 7c) which are derived from hydroquinone, as well as the appropriate amount of repeating units of the formulae 7d) and, in addition, repeating units 7f).

Other preferred polyester amides contain 5 to 20 mol-% of units 7a), 5 to 20 mol-% of units 7b) which are derived from m-aminobenzoic acid, as well as 5 to 20 mol-% of repeating units 7c) which are derived from hydroquinone and 4,4'-dihydroxydiphenyl, as well as the appropriate amount of repeating units of the formulae 7d) and, in addition, repeating units 7f).

Further preferred polyester amides contain 5 to 20 mol-% of units 7a), 5 to 20 mol-% of units 7b) which are derived from m-aminobenzoic acid, and 5 to 20 mol-% of units 7c) which are derived from hydroquinone, as well as the appropriate amount of repeating units of the formulae 7d) and, in addition, repeating units 7f).

Polyester amides of type 7 are described in EP-A 230,546.

8. Polyester amides composed of 8a) 3 to 30 mol-%, in particular 5 to 25 mol-%, of repeating units of the formula

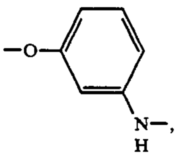

m-aminophenol is a suitable starting compound;

8b) 3 to 25 mol-%, preferably 5 to 20 mol-%, of at least one of the repeating units of the formulae

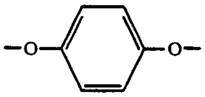

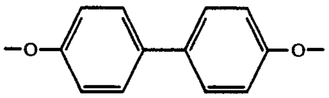

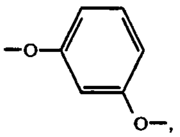

examples of suitable starting compounds are hydroquinone, 4,4'-dihydroxybiphenyl and resorcinol. Particularly preferred repeating units are derived from hydroquinone or 4,4'-dihydroxydiphenyl or mixtures thereof, 8c) a molar amount equivalent to the total of components 8a) and 8b) of repeating units of the formulae

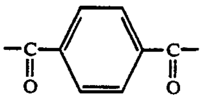

-continued

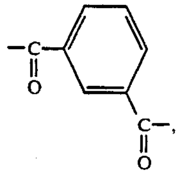

examples of suitable starting compounds are terephthalic acid and isophthalic acid, 8d) repeating units derived from p-hydroxybenzoic acid, advantageously in an amount of at least 10 mol-%, in particular at least 20 mol-%;

8e) where appropriate from 5 to 25 mol-%, in particular 5 to 15 mol-%, of repeating units of the formula

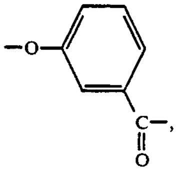

an example of a suitable starting compound is m-hydroxybenzoic acid.

Polyester amides with these units are described in EP-A 226,080.

9. Polyester imides composed of 9a) 5 to 35 mol-%, in particular 7 to 31 mol-%, of repeating units of the formulae

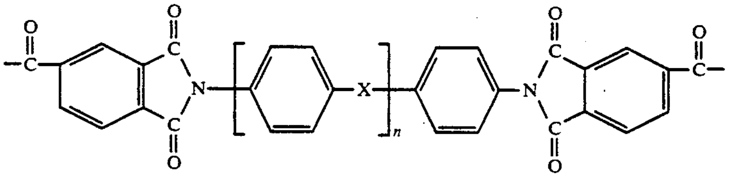

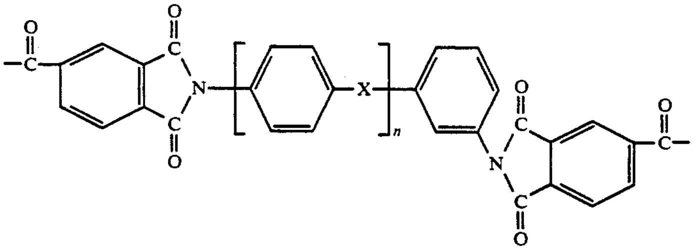

X and n can each vary. X is —O—, —S—, $—SO_2—$, —CO—, $—CH_2—$ or $C(CH_3)_2—$, in particular —O—, $—SO_2—$ or $—CH_2—$, and n is 0 or 1, in particular 1; examples of suitable starting compounds are 4,4'-di(4-carboxy-N-phthalimido)diphenyl ether,
4,4'-di(4-carboxy-N-phthalimido)diphenylmethane,
4,4'-di(4-carboxy-N-phthalimido)diphenyl sulfone,
4,4'-di(4-carboxy-N-phthalimido)diphenyl sulfide,
4,4'-di(4-carboxy-N-phthalimido)diphenyl ketone,
3,4'- or 3,3'-di(4-carboxy-N-phthalimido)diphenyl ether,
3,4'- or 3,3'-di(4-carboxy-N-phthalimido)diphenyl sulfide,
3,4'- or 3,3'-di(4-carboxy-N-phthalimido)diphenyl sulfone,
3,4'- or 3,3'-di(4-carboxy-N-phthalimido)diphenyl ketone,
3,4'- or 3,3'-di(4-carboxy-N-phthalimido)diphenylmethane;

(processes for the preparation of such compounds are described in Polymer Science (A-1), Vol. 7, pages 320-332);

9b) 0 to 30 mol-%, in particular 0 to 20 mol-%, of repeating units of the formulae

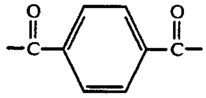 or 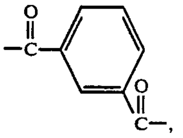

suitable starting compounds for these units are terephthalic acid and isophthalic acid;

9c) a molar amount equivalent to the total of components 9a) and 9b) of at least one of the repeating units of the following formulae

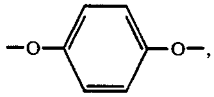

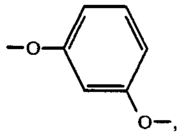

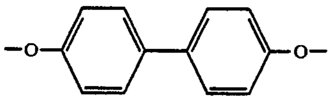 or

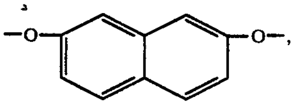

examples of suitable starting compounds are hydroquinone, resorcinol, 4,4'-dihydroxybiphenyl and 2,7-dihydroxynaphthalene;

9d) at least 10 mol-%, in particular at least 20 mol-%, of repeating units of the formula

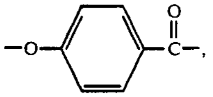

an example of a suitable starting compound is p-hydroxybenzoic acid;

9e) where appropriate 5 to 25, in particular 10 to 20, mol-% of repeating units of the formula

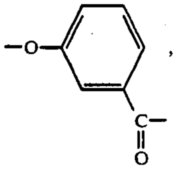

an example of a suitable starting compound is m-hydroxybenzoic acid.

Preferred polyester imides contain as component 9c) 10 to 31 mol-% of repeating units which are derived from hydroquinone, and/or 5 to 25 mol-% of repeating units which are derived from the other starting compounds listed under 9c). Particularly preferred components 9c) are repeating units derived from hydroquinone, resorcinol and/or 4,4'-dihydroxydiphenyl and mixtures thereof.

Polyester imides of the abovementioned type are described in EP-A 227,947.

10. Polyester amide imides composed of 10a) 5 to 35 mol-%, in particular 7 to 25 mol-%, of repeating units of the formulae

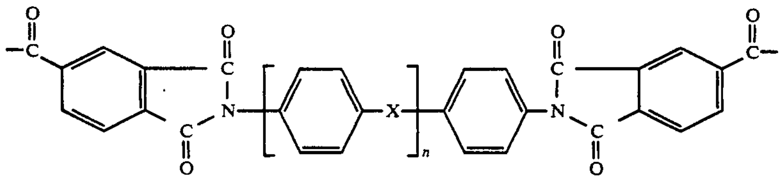

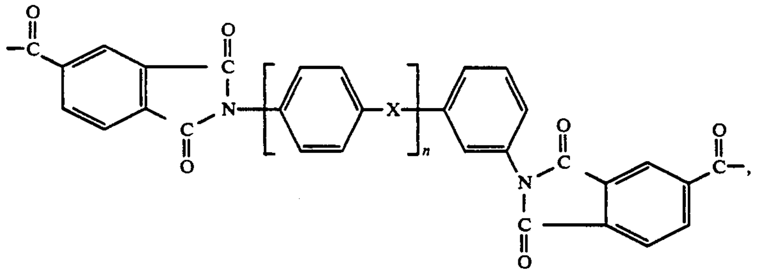

where suitable starting compounds are the same as those mentioned above for units 9a) of the polyester imides 9); compounds of the formula I and II can be obtained, for example, as described in Polym. Sci. (A-1), 7 (1969) 320-332

10b) 0 to 30 mol-%, in particular 0 to 20 mol-%, of repeating units of the formulae

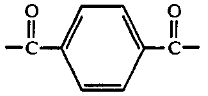 and/or 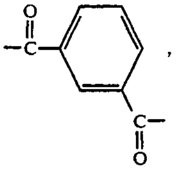 , where examples of suitable starting compounds are terephthalic acid and isophthalic acid;

10c) a molar amount equivalent to the total of components 10a) and 10b) of at least one of the repeating units of the following formulae

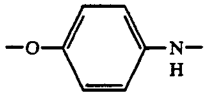

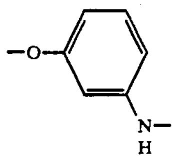

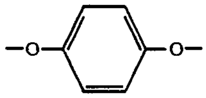

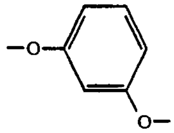

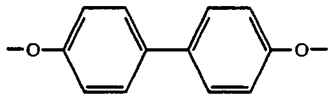

where starting compounds which may be mentioned are p-aminophenol, m-aminophenol, hydroquinone, resorcinol and 4,4'-dihydroxydiphenyl;

10d) where appropriate 5 to 25 mol-%, in particular 5 to 20 mol-%, of at least one of the repeating units of the formulae

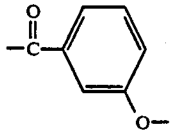

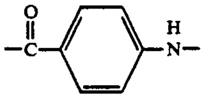

-continued

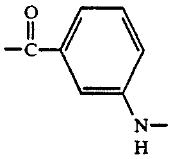

where suitable starting compounds are m-hydroxybenzoic acid, p-aminobenzoic acid and m-aminobenzoic acid;

10e) repeating units, in particular in an amount of at least 10 mol-%, of the formula

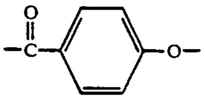

where p-hydroxybenzoic acid may be mentioned as a suitable starting compound.

It is obvious that the total of the molar percentages of components 10a) to 10e) is 100 mol-% in each case.

The polyester amide imides according to the invention advantageously contain as component 10c) 5 to 20 mol-% of repeating units derived from m-aminophenol, and/or 2 to 8 mol-% of repeating units derived from p-aminophenol and/or 5 to 20 mol-% of at least one of the repeating units derived from hydroquinone, resorcinol and 4,4'-dihydroxydiphenyl.

Particularly preferred polyester amide imides contain as component 10c) 5 to 20 mol-% of repeating units derived from m-aminophenol, and 5 to 15 mol-% of repeating units derived from hydroquinone and, where appropriate, 5 to 15 mol-% of repeating units derived from 4,4'-dihydroxydiphenyl.

Polymers of type 10 are described in EP-A 230,547.

11. Polyester imides composed of 11a) 5 to 35 mol-%, in particular 7 to 25 mol-%, of repeating units of the formulae

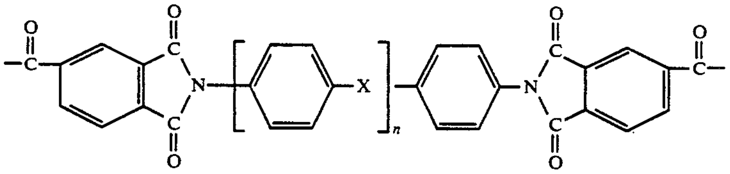

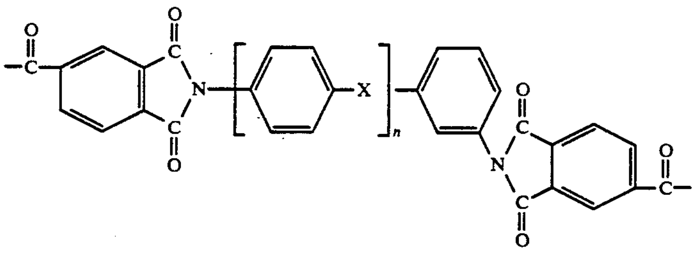

where X may vary and is, in each case, —O—, —S—, $—SO_2—$, —CO—, $—CH_2$ or $—C(CH_3)_2—$, and n is 0 or 1;

suitable starting compounds are listed for units 9a) for polymers of type 9;

the preparation of starting compounds of this type is described, for example, in J. Polym. Sci. (A-1), 7 (1969) 321–332;

11b) 0 to 30 mol-%, in particular 0 to 20 mol-%, of repeating units of the formulae

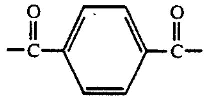 and/or 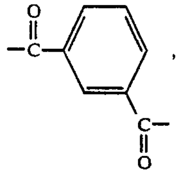, where terephthalic acid and isophthalic acid may be mentioned as starting compounds;

11c) a molar amount equivalent to the total of components 11a) and 11b) of aromatic dihydroxy compounds, namely 3 to 35 mol-% of repeating units of the formula

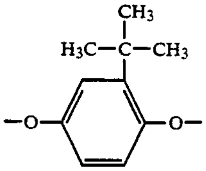

where tert.-butylhydroquinone can be used as suitable starting compound, as well as at least one of the following repeating units in an amount of from 2 to 25 mol-%

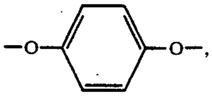,

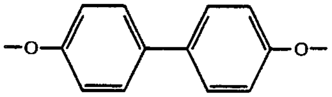

where hydroquinone and 4,4'-dihydroxydiphenyl may be mentioned as starting compounds, as well as 0 to 25 mol-% of repeating units of the formula

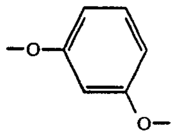

where resorcinol may be mentioned as suitable starting compound;

11d) where appropriate 5 to 25 mol-%, in particular 5 to 20 mol-%, of repeating units of the formula

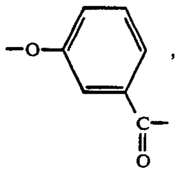

an example of a suitable starting compound is m-hydroxybenzoic acid;

11e) repeating units of the following formula, advantageously in an amount of not less than 10 mol-%

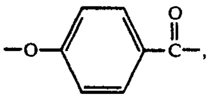

where p-hydroxybenzoic acid can be employed as starting compound.

It is obvious that the total of the molar proportions of components 11a), 11b), 11c), 11d) and 11e) is 100 mol-% in each case.

Advantageous polyester imides contain as components 11c) 5 to 25 mol-% of repeating units derived from t-butylhydroquinone, and 5 to 20 mol-% of at least one of the repeating units derived from hydroquinone, resorcinol or 4,4'-dihydroxydiphenyl.

Further preferred sorts of polyester imides of type 11 are described in EP-A 225,537.

12. Polyester amide imides composed of 12a) 5 to 35 mol-% of repeating units of the formula

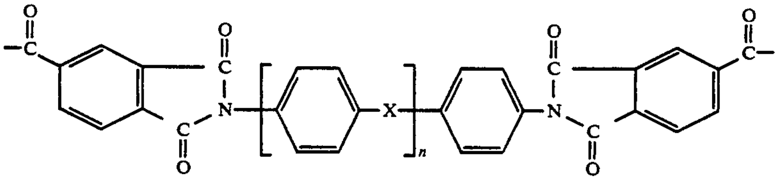

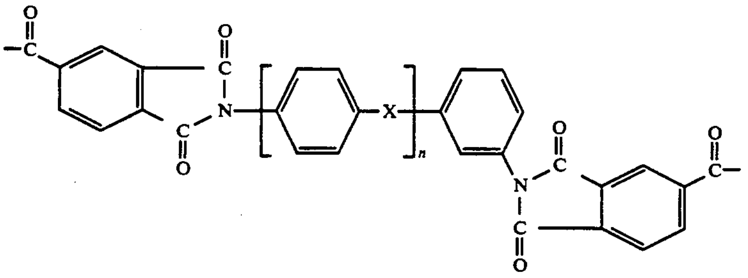

where X and n have the meanings described above for units 9a) in polymers 9;

12b) 0 to 30 mol-% of repeating units derived from terephthalic acid and/or isophthalic acid;

12c) a molar amount equivalent to the total of components 12a) and 12b) of at least one of the following repeating units 12c1) 3 to 35 mol-% of units of the formula

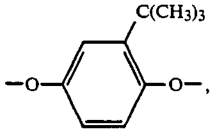

12c2) 0 to 10 mol-% of units of the formula

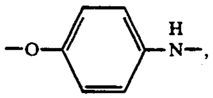

12c3) 2 to 25 mol-% of units of the formula

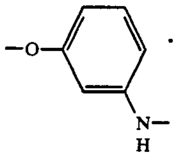

12c4) 2 to 20 mol-% of units of the formula

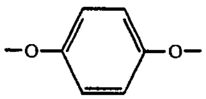

12c5) 0 to 20 mol-% of units of the formula

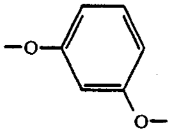

and

12c6) 2 to 20 mol-% of units of the formula

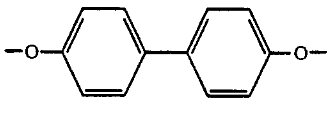

where suitable starting compounds are t-butylhydroquinone, p-aminophenol, m-aminophenol, hydroquinone, resorcinol and 4,4'-dihydroxydiphenyl;

12d) at least 10 mol-% of repeating units of the formula

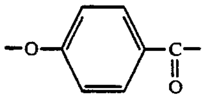

where a starting compound which may be mentioned is p-hydroxybenzoic acid; and 12e) 0 to 25 mol-% of at least one of the repeating units of the formula

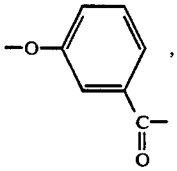

,

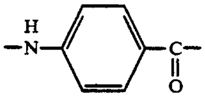

or

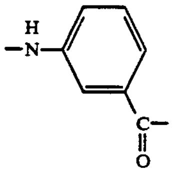

where these units are derived from m-hydroxybenzoic acid, p-aminobenzoic acid and m-aminobenzoic acid.

Polyester amide imides of type 12 are described in EP-A 225,529.

13. Polyether ester imides composed of 13a) 5 to 35 mol-% of repeating units of the formula

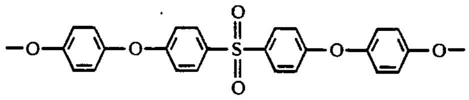

where 4,4'-di(p-hydroxyphenoxy)diphenyl sulfone may be mentioned as suitable starting compound;

13b) 5 to 35 mol-% of repeating units of the formulae

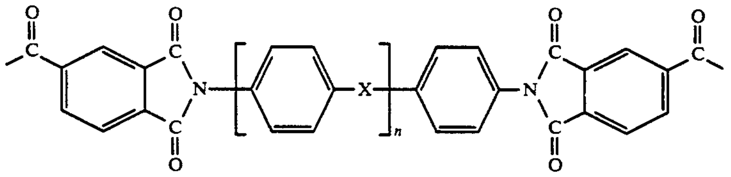

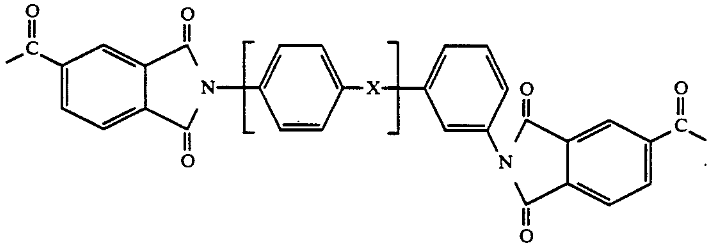

where X is a chemical bond, —O—, —S—, —$SO_2$—, —CO—, —$CH_2$— or =$C(CH_3)_2$ and n is 0 or 1; suitable starting compounds are listed under units 9a) in polymers of type 9;

13c) 15 to 30 mol-% of repeating units derived from terephthalic acid, 13d) a molar amount equivalent to the total of components 13b) plus 13c) minus 13a) of repeating units of the formulae

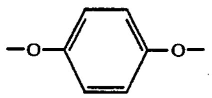

and/or

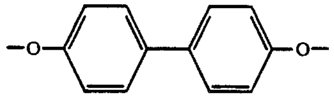

which are derived from hydroquinone and/or 4,4,'-dihydroxydiphenyl, 13e) repeating units derived from p-hydroxybenzoic acid.

It is obvious that the molar percentages of components 13a) to 13e) total 100 mol-% in each case.

Preferred polyether ester imides are composed of 10 to 30 mol-% of repeating units 13a)

10 to 30 mol-% of repeating units 13b)

15 to 30 mol-% of repeating units 13c)

a molar amount equivalent to the total of 13b) plus 13c)

minus 13a) of repeating units 13d), and repeating units of the formula 13e).

Particularly appropriate polyether ester imides have proved to be those composed of 15 to 25 mol-% of repeating units 13a), 15 to 25 mol-% of repeating units 13b), 20 to 30 mol-% of repeating units 13c), a molar amount equivalent to a total of 13b) plus 13c) minus 13a) of repeating units 13d), in particular those derived from hydroquinone, and repeating units 13e), advantageously in an amount of at least 10 mol-%.

Thermotropic polymers of this type are described in EP-A 231,642.

14. Mesomorphic polycondensates composed of 14a) at least 10 mol-%, advantageously at least 20 mol-%, of repeating units derived from p-hydroxybenzoic acid, 14b) 5 to 30 mol-%, advantageously 10 to 25 mol-%, of repeating units derived from methylhydroquinone, 14c) 0 to 20 mol-%, in particular 2 to 18 mol-%, of at least one of the repeating units of the formulae

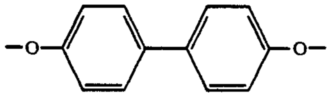

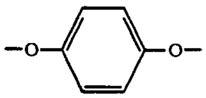

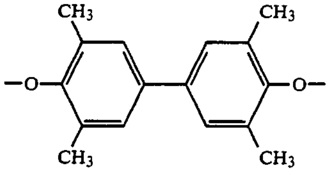

where 4,4'-dihydroxy-diphenyl, hydroquinone and 3,3',5,5'-tetramethyl-4,4'-dihydroxydiphenyl may be mentioned as starting compounds, 14d) 0 to 20 mol-%, advantageously 2 to 15 mol-%, of at least one of the repeating units of the following formulae

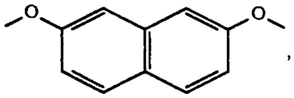,

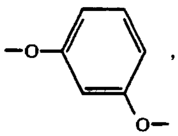,

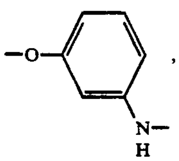,

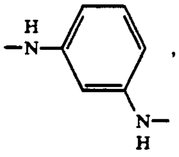, where 2,7-dihydroxynaphthalene, resorcinol, m-aminophenol and m-phenylenediamine may be mentioned as starting compounds, 14e) a molar amount equivalent to the total of components 14b), 14c) and 14d) of repeating units derived from terephthalic acid, where the total of molar percentages of components 14a), 14b), 14c), 14d) and 14e) is 100 mol-% in each case It is also possible for a portion, eg. up to 50% of the required molar amount, of the units derived from terephthalic acid to be replaced by repeating units derived from isophthalic acid.

It is furthermore possible for a portion of components 14a), eg. up to an amount of 15 mol-%, to be replaced by at least one of the repeating units of the following formulae

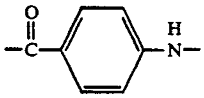

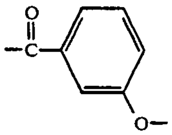

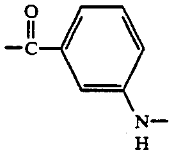

Suitable starting compounds are p-aminobenzoic acid, m-hydroxybenzoic acid and m-aminobenzoic acid.

Products of this type are described in EP-A 230,550.

15. Liquid-crystalline polycondensates which contain carbamide groups and are composed of 15a) aromatic hydroxy and/or amino carboxylic acids in which the hydroxyl or amino group is not vicinal to the carboxyl group 15b) 0.1 to 20 mol-% of urea 15c) aromatic dihydroxy, diamino and/or hydroxy amino compounds in which the hydroxyl and amino groups are not vicinal to one another 15d) a molar amount equivalent to the total of components b and c of aromatic dicarboxylic acids in which the carboxyl groups are not vicinal.

Preferred polymers of this type contain 15a) at leasts 10 mol-% of at least one of the repeating units

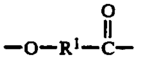 or 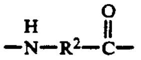

where $R^1$ and $R^2$ can be identical or different and each is 1,4-phenylene, 1,3-phenylene, 2,7-naphthylene or 2,6-naphthylene 15b) 0.1 to 20 mol-% of repeating units of the formula

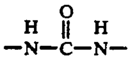

15c) at least one of the repeating units of the formula

—X—R³—Y— where $R^3$ is 1,4-phenylene, 1,3-phenylene, 2,6-naphthylene, 2,7-naphthylene, 4,4'-biphenylylene, 3,4'-biphenylylene, 2,6-anthraquinonylene, it being possible for the radicals to be substituted by halogens, alkyls of up to 4 carbons or a phenyl, and $R^3$ is also

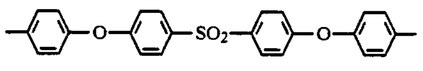

and X and Y can be identical or different and each is oxygen or —NH—, 15d) an amount equivalent to the total of components 15b) and 15c) of repeating units of the formula

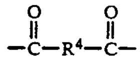

where $R^4$ is 1,4-phenylene, 1,3-phenylene or the following

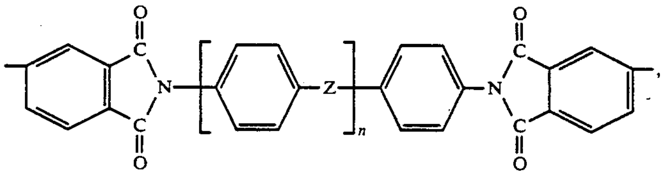

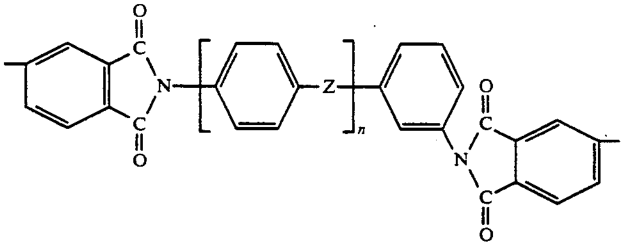

where Z is —O—, —S—, $—SO_2—$, —CO—, $—CH_2—$, $=C(CH_3)_2$ in each case, and n is 0 or 1, or $R^4$ is also

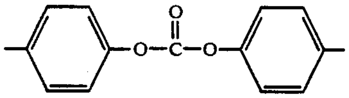

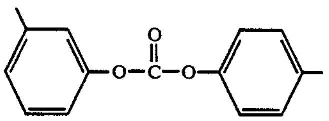

and

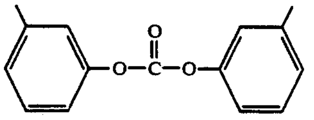

Examples of preferred polycondensates of this type are 15/1. completely aromatic mesomorphic polyether ester carbamides composed of 15a) at least 10 mol-% of 4-hydroxybenzoic acid 15b) 0.5 to 12 mol-% of urea $15c_1$) 3 to 20 mol-% of hydroquinone and/or 4,4'-dihydroxydiphenyl, $15c_2$) 5 to 30 mol-% of 4,4'-di(p-hydroxyphenoxy)-diphenyl sulfone and 15d) a molar amount equivalent to the total of components 15b) and 15c) of terephthalic acid.

15/2. Polyester carbamides composed of 15a) at least 10 mol-% of 4-hydroxybenzoic acid 15b) 0.1 to 11 mol-% of urea $15c_1$) 10 to 25 mol-% of 3,3',5,5'-tetramethyl-4,4'-dihydroxydiphenyl $15c_2$) 5 to 15 mol-% of hydroquinone $15c_3$) 5 to 15 mol-% of 4,4'-dihydroxydiphenyl and 15d) a molar amount equivalent to the total of components 15b) and 15c) of terephthalic acid.

15/3. Polyester carbamides composed of 15a) at least 10 mol-% of 4-hydroxybenzoic acid 15b) 0.1 to 7 mol-% of urea $15c_1$) 5 to 35 mol-% of tert.-butylhydroquinone $15c_2$) 2 to 30 mol-% of 4,4'-dihydroxydiphenyl and 15d) a molar amount equivalent to the total of 15b) and 15c) of terephthalic acid.

15/4. Polyester amide carbamides composed of 15a) at least 10 mol-% of 4-hydroxybenzoic acid which can in part be replaced by 4-aminobenzoic acid 15b) 0.4 to 10 mol-% of urea $15c_1$) 3 to 30 mol-% of tert.-butylhydroquinone $15c_2$) 3 to 30 mol-% of 3-aminophenol $15c_3$) 2 to 25 mol-% of at least one of hydroquinone, 4,4'-dihydroxyiiphenyl and resorcinol, and 15d) a molar amount equivalent to the total of components 15b) and 15c) of terephthalic acid which can be in part replaced by isophthalic acid.

15/5. Polyester amide carbamides composed of 15a) at least 10 mol-% of 4-hydroxybenzoic acid and, where appropriate, 5 to 25 mol-% of 3-hydroxybenzoic acid 15b) 0.1 to 7 mol-% of urea $15c_1$) 3 to 30 mol-% of 3-aminophenol $15c_2$).3 to 25 mol-% of at least one of hydroquinone, 4,4'-dihydroxydiphenyl or resorcinol and 15d) a molar amount equivalent to the total of components 15b) and 15c) of terephthalic acid and/or isophthalic acid.

15/6. Polyether ester carbamides composed of 15a) at least 10 mol-% of 4-hydroxyb-enzoic acid 15b) 0.1 to 7 mol-% of urea 15c$_1$) 5 to 20 mol-% of 4,4'-di(p-hydroxyphenoxy)-diphenyl sulfone 15c$_2$) 10 to 30 mol-% of tert.-butylhydroquinone and 15d) a molar amount equivalent to the total of components 15b) and 15c) of terephthalic acid.

15/7. Polyether ester imide carbamides composed of 15a) at least 10 mol-% of 4-hydroxybenzoic acid 15b) 0.1 to 5 mol-% of urea 15c$_1$) 5 to 35 mol-% of 4,4'-di(p-hydroxyphenoxy)-diphenyl sulfone 15c$_2$) a molar amount equivalent to the total of components $(d1+d2)-(c_1+b)$ of hydroquinone and/or 4,4'-dihydroxydiphenyl and 15d$_1$) 5 to 35 mol-% of 4,4'-bis(4-carboxy-N-phthalimido)diphenyl ether, -methane, sulfone, sulfide or ketone and 15d$_2$) 15 to 30 mol-% of terephthalic acid.

15/8. Polyester carbamides composed of 15a) at least 20 mol-% of 4-hydroxybenzoic acid 15b) 1 to 10 mol-% of urea 15c$_1$) 5 to 15 mol-% of tert.-butylhydroquinone 15c$_2$) 5 to 15 mol-% of 4,4'-dihydroxydiphenyl and 15d) a molar amount equivalent to the total of components 15b) and 15c) of terephthalic acid.

It is obvious that the total of the components in the abovementioned polycondensates is 100 mol-% in each case.

Polymers of these structures are described in EPA 231,468.

16. Completely aromatic mesomorphic polyesters which below 300° C. form a liquid-crystalline filament-forming melt essentially composed of 16a) 5 to 25 mol-% of repeating units of the formula

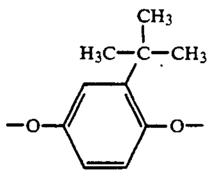

16b) 5 to 25 mol-% of repeating units of the formula

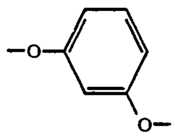

16c) 10 to 50 mol-% of repeating units of the formula

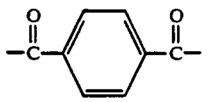

and 16d) at least 10 mol-% of repeating units of the formula

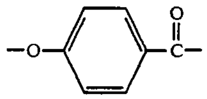

where the total of the molar proportions of components 16a), 16b), 16c) and 16d) is 100 mol-% in each case and the molar ratio of components 16a) and 16b) to component 16c) is in the range from 0.9:1 to 1.1:1.

Starting compounds which may be mentioned for the various units are t-butylhydroquinone, resorcinol, terephthalic acid and p-hydroxybenzoic acid.

17. Thermotropically mesomorphic polyesters composed of 17a) at least 10 mol-% of units derived from p-hydroxybenzoic acid, 17b) 1 to 25 mol-% of repeating units of the formula

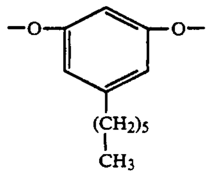

17c) 5 to 20 mol-% of at least one of the repeating units of the following formulae

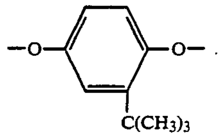

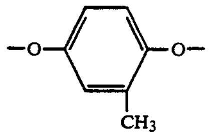

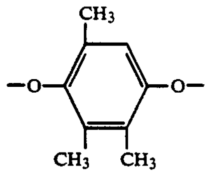

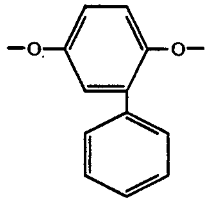

-continued

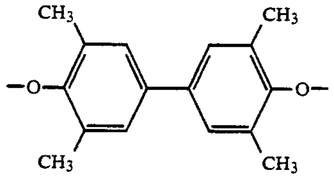

17d) 5 to 15 mol-% of repeating units of the formula

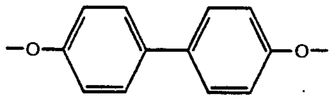

17e) 10 to 60 mol-% of repeating units of the formula

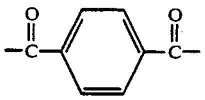

where the total of the molar proportions of 17a), 17b), 17c) and 17e) is 100 mol-% in each case and the molar ratio of components 17b)+17c)+17d) to component 17e) is in the range from 0.9:1 to 1.1:1.

Preferred starting material are as follows for repeating units of the formula 17b) 3-n-hexylresorcinol, 17c) t-butylhydroquinone, methylhydroquinone, trimethylhydroquinone, phenylhydroquinone and 3,3',5,5'-tetramethyl-4,4'-dihydroxydiphenyl 17d) 4,4'-dihydroxydiphenyl 17e) terephthalic acid.

18. Completely aromatic thermotropically mesomorphic polyesters based on 18a) 30 to 60 mol-% of 4-hydroxybenzoic acid 18b) 20 to 35 mol-% of a mixture of $b_1$) terephthalic acid and $b_2$) isophthalic acid where the molar ratio of $b_1$ to $b_2$ is in the range from 1.04:1 to 19:1, preferably from 1.5:1 to 10:1, and 18c) 20 to 35 mol-% of a mixture of $18c_1$) hydroquinone $18c_2$) 4,4'-dihydroxydiphenyl and $18c_3$) 0 to 5 mol-% of a dihydroxy compound of the general formula

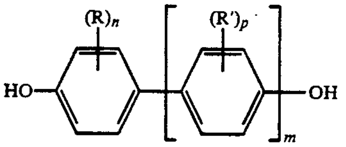

where R and R' are alkyls of up to 4 carbons, halogen or an aryl, n and p are 1, 2 or 3, and m is 0 or 1, the molar ratio of $18c_1$) to $18c_2$) is in the range from 0.1:1 to 2.67:1, preferably from 0.5:1 to 2.33:1, and the molar ratio of 18b) to 18c) is in the range from 0.9:1 to 1.1:1, preferably from 0.98:1 to 1.02:1.

The total of components 18a)+18b)+18c) is always 100 mol-%.

19. Completely aromatic thermotropically mesomorphic polyesters based on 19a) 30 to 60 mol-% of 4-hydroxybenzoic acid 19b) 20 to 35 mol-% of a mixture of $19b_1$) terephthalic acid and $19b_2$) isophthalic acid where the molar ratio of $19b_1$) to $19b_2$) is in the range from 1.04:1 to 19:1, preferably from 1.5:1 to 10:1, and 19c) 20 to 35 mol-% of a mixture of $19c_1$) hydroquinone $19c_2$) 4,4'-dihydroxydiphenyl and $19c_3$) 0.5 to 5 mol-% of $19c_{31}$) 2,7-dihydroxynaphthalene and/or $19c_{32}$) 1,3-dihydroxybenzene and/or $19c_{33}$) an aromatic dihydroxy compound of the general formula

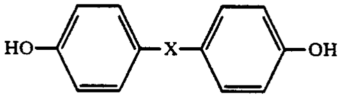

where X is $-CH_2-$, $-C(CH_3)_2-$, $-S-$, $-SO_2-$, $-O-$ or $-CO-$, or the derivatives thereof substituted in the nucleus by chlorine, bromine, aryl or $C_1$–$C_8$-alkyl or alkoxy, and/or $19c_{34}$) a compound of the general formula

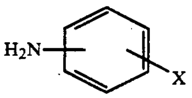

where X is $-NH_2$ or $-OH$ and the substituents are meta or para with respect to one another, or the derivatives thereof which are substituted in the nucleus by chlorine, bromine, aryl or $C_1$–$C_8$-alkyl or alkoxy, where the molar ratio of $19c_1$) to $19c_2$) is in the range from 0.1:1 to 2.67:1, preferably from 0.5:1 to 2.33:1, and the molar ratio of 19b) to 19c) in the range from 0.9:1 to 1.1:1, preferably from 0.98:1 to 1.02:1.

20. Completely aromatic thermotropically mesomorphic polyesters based on 20a) 25 to 60 mol-% of a mixture of $20a_1$) 4-hydroxybenzoic acid and $20a_2$) 3-hydroxybenzoic acid, 4-aminobenzoic acid and/or 3-aminobenzoic acid or the derivatives thereof substituted in the nucleus by chlorine, bromine, $C_1$–$C_8$-alkyl or $C_1$–$C_8$-alkoxy, where the molar ratio of $20a_1$) to $20a_2$) is in the range from 5:1 to 41:1, preferably from 6:1 to 20:1, 20b) 20 to 37.5 mol-% of a mixture of $20b_1$) terephthalic acid and $20b_2$) isophthalic acid where the molar ratio of $20b_1$) to $20b_2$) is in the range from 1.04:1 to 19:1, preferably from 1.5:1 to 10:1, and 20c) 20 to 37.5 mol-% of a mixture of $20c_1$) hydroquinone $20c_2$) 4,4'-dihydroxyiiphenyl where the molar ratio of $20c_1$) to $20c_2$) is in the range from 0.1:1 to 2.67:1, preferably from 0 5:1 to 2.33:1, and the molar ratio of 20b) to 20c) is in the range from 0.9:1 to 1.1:1, preferably from 0.98:1 to 1.02:1.

21. Completely aromatic thermotropically mesomorphic polyesters based on 21a) 30 to 60 mol-% of 4-hydroxybenzoic acid 21b) 20 to 35 mol-% of a mixture of 21b₁) terephthalic acid and 21b₂) isophthalic acid 21b₃) 0.5 to 5 mol-% of a dicarboxylic acid of the general formula

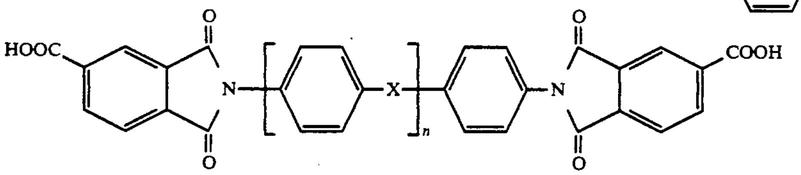

where X is —O—, —S—, —$SO_2$—, —CO—, —$CH_2$— or —$C(CH_3)_2$—, n is 0 or 1, and the two imide nitrogens are meta or para to X, or the derivatives thereof substituted in the nucleus by $C_1$–$C_8$-alkyl, $C_1$–$C_8$-alkoxy, aryl, chlorine or bromine and where the molar ratio of 21b₁) to 21b₂) is in the range from 1.04:1 to 19:1, preferably from 1 5:1 to 10:1, and 21c) 20 to 35 mol-% of a mixture of 21c₁) hydroquinone 21c₂) 4,4'-dihydroxydiphenyl where the molar ratio of 21c₁) to 21c₂) is in the range from 0.1:1 to 2.67:1, preferably from 0.5:1 to 2.33:1, and the molar ratio of 21b) to 21c) is in the range from 0.9:1 to 1.1:1, preferably from 0.98:1 to 1.02:1.

Suitable starting compounds 21b₃) which may be mentioned are the compounds listed under the unit 9a) for the polymers of type 9 described above.

22. Thermotropically mesomorphic completely aromatic polyesters based on 22a) 30 to 60 mol-% of 4-hydroxybenzoic acid, 22b) 20 to 35 mol-% of terephthalic acid and 22c) 20 to 35 mol-% of a mixture of 22c₁) trimethylhydroquinone and 22c₂) resorcinol in the molar ratio of 22c₁) to 22c₂) of 0.4:1 to 0.7:1, preferably of 0.45:1 to 0.65:1, and the molar ratio of 22b) to 22c) is in the range from 0.9:1 to 1.1:1, preferably from 0.98:1 to 1.02:1.

23. Completely aromatic thermotropically mesomorphic polyesters based on 23a) 3 to 15 mol-% of units derived from hydroquinone, 23b) 5 to 35 mol-%, in particular 25 to 35 mol-%, of units derived from 2,7-dihydroxynaphthalene, 23c) a molar amount equivalent to the total of 23a) and 23b) of units derived from terephthalic acid, and 23d) 10 to 70 mol-%, in particular 10 to 39.4 mol-%, of units derived from p-hydroxybenzoic acid.

A portion of the repeating units 23a) and 23b) can be replaced by one or more units derived from 23e) 4,4'-dihydroxydiphenyl and/or 23f) 4,4'-dihydroxydiphenyl sulfone and/or 23g) 2,2-di(4-hydroxy-phenyl)propane.

It is advantageous for the content of repeating units 23e), 23f) and/or 23g) to be 2 to 20 mol-%.

Particularly preferred polyesters contain 25 to 40 mol-% of repeating units 23b) as well as of one or more repeating units 23e), 23f) and/or 23g).

Products of this type are described in EP-A 139,303.

24. Completely aromatic thermotropically mesomorphic polyesters composed of 24a) 10 to 90 mol-% of repeating units of the formula

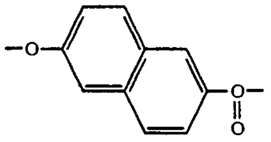

(a suitable starting compound is, for example, 2-hydroxy6-carboxynaphthalene), and 24b) 10 to 90 mol-% of repeating units of the formula

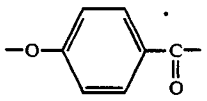

(a suitable starting compound is, for example, p-hydroxybenzoic acid).

Completely aromatic polyesters of this type advantageously contain the repeating units 24a) in an amount of from 65 to 85 mol-% and particularly preferably in amounts of from 70 to 80 mol-%.

25. Completely aromatic thermotropically mesomorphic polyesters composed of 25a) 30 to 70 mol-%, in particular 40 to 60 mol-%, of repeating units of the formula

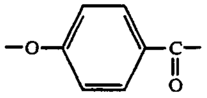

(a suitable starting compound is, for example p-hydroxybenzoic acid);

25b) 20 to 30 mol-% of repeating units of the formula

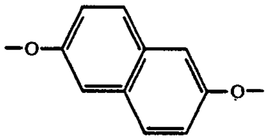

(a suitable starting compound is, for example, 2,6-dihydroxynaphthalene) and 25c) 20 to 30 mol-% of repeating units of the formula

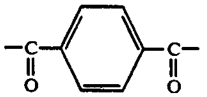

(a suitable starting compound is, for example, terephthalic acid).

It is obvious that the repeating units can also be substituted by one or more alkyl or alkoxy of up to 4 carbons, halogen, phenyl or combinations thereof.

26. Thermotropically mesomorphic polyesters composed of 26a) 20 to 60 mol-%, in particular 25 to 45 mol-%, of repeating units of the formula

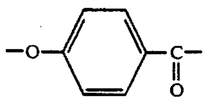

(a suitable starting compound is, for example, p-hydroxybenzoic acid), 26b) 5 to 18 mol-% of repeating units of the formula

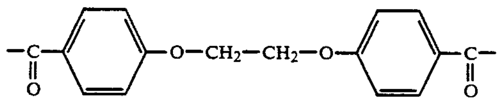

(a suitable starting compound is, for example, 1,2-di(4-carboxyphenoxy)ethane), 26c) 5 to 35 mol-% of repeating units of the formula

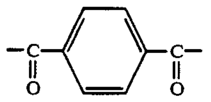

(a suitable starting compound is, for example, terephthalic acid), and 26d) 20 to 40 mol-% of repeating units of the formula

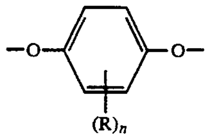

where R is, in each case, methyl, chlorine or bromine or combinations thereof, and n is 1, 2 or 3.

Preferred polyesters contain 35 to 45 mol-% of repeating units 26a), 10 to 15 mol-% of repeating units 26b), 15 to 25 mol-% of repeating units 26c) and 25 to 35 mol-% of repeating units 26d).

It is obvious that the total of components 26b) and 26c) is equimolar to the amount of component 26d).

It is also possible for components 26a), 26b) and 26c) to be substituted by one or more alkyl or alkoxy of up to 4 carbons, halogen, phenyl or combinations thereof. 27. Thermotropically mesomorphic polyesters composed of 27a) 20 to 40 mol-%, in particular 20 to 30 mol-%, of repeating units of the formula

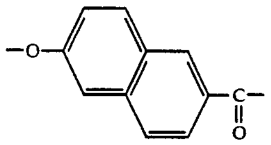

(a suitable starting compound is, for example, 2-hydroxy6-naphthalenecarboxylic acid), 27b) 10 to 50 mol-%, in particular 25 to 40 mol-%, of repeating units of the formula

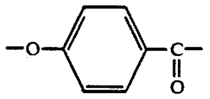

(a suitable starting compound is, for example, p-hydroxybenzoic acid), 27c) 5 to 30 mol-%, in particular 15 to 25 mol-%, of repeating units of the formula

—O—R'—O— where R' is a divalent radical having at least one phenyl ring, and 27d) 5 to 30 mol-%, in particular 15 to 25 mol-%, of repeating units of the formula

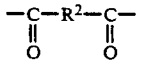

where $R^2$ is a divalent radical having at least one phenyl ring.

The preferred starting compound for 27c) is hydroquinone and for 27d) is terephthalic acid.

It is obvious that the repeating units can also have one or more alkyl or alkoxy of up to 4 carbons, halogen, phenyl or combinations thereof.

28. Thermotropically mesomorphic polyesters composed of 28a) 10 to 90 mol-%, in particular 10 to 40 mol-%, of repeating units of the formula

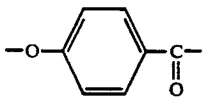

(a suitable starting compound is, for example, 2-hydroxy6-naphthalenecarboxylic acid), 28b) 5 to 45 mol-%, in particular 10 to 40 mol-%, of repeating units of the formula

—O—R'—O— where R' is a divalent radical having at least one phenyl ring (a suitable starting compound is hydroquinone), and 28c) 5 to 45 mol-%, in particular 10 to 40 mol-%, of repeating units of the formula

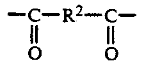

where $R^2$ is a divalent radical having at least one phenyl ring (a preferred starting compound is terephthalic acid).

Other preferred polyesters contain 60 to 80 mol-% of units 28a), 10 to 20 mol-% of 28b) and 10 to 20 mol-% of units 28c). It is obvious that the repeating units can also be substituted by one or more alkyl or alkoxy of up to 4 carbons, halogen, phenyl or combinations thereof.

29. Thermotropically mesomorphic polyester amides composed of

29a) .10 to 90 mol-% of repeating units of the formula

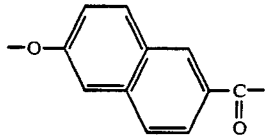

(a suitable starting compound is 2-hydroxy-6-naphthalenecarboxylic acid), 29b) 5 to 45 mol-% of repeating units of the formula

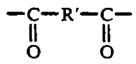

where R′ is a divalent radical consisting of at least one phenyl ring or is a divalent trans-cyclohexane ring (a preferred starting compound is terephthalic acid), 29c) 5 to 45 mol-% of repeating units of the formula $$—Y—R^2—Z—$$

where $R^2$ is a divalent radical consisting of at least one phenyl ring, Y is —O—, —NH— or —$NR^3$— and Z can be —NH— or —$NR^3$—, and $R^3$ is an alkyl of up to 6 carbons or a phenyl (preferred starting compounds for 29c) are 4-aminophenol or p-phenylenediamine), and 29d) 0 to 40 mol-% of repeating units of the formula $$—O—R^4—O—$$

where $R^4$ is a divalent radical consisting of at least one phenyl ring (a preferred starting compound is hydroquinone).

It is obvious that the repeating units can also be substituted by one or more alkyl or alkoxy of up to 4 carbons, halogen, phenyl or combinations thereof.

It is also possible in general for the thermotropically mesomorphic polymers to contain repeating units which allow branching points to be formed Examples of suitable starting compounds are 1,3,5-trihydroxybenzene, 3,5-dihydroxybenzoic acid or 5-hydroxyisophthalic acid. Polymers of this type are described, for example, in German Laid-Open Application DOS 3,346,549.

A block system is also possible for the polymers, in which case the polymer chains are composed of one or more blocks able to form mesomorphic melts and of one or more blocks of a thermoplast which is not thermotropically mesomorphic.

It is additionally possible to employ mixtures of various thermotropically mesomorphic polymers or blends of thermotropically mesomorphic polymers and other thermoplastic polymers or block copolymers composed of one or more blocks able to form a mesomorphic melt and of one or more blocks of a thermoplastic which is not thermotropically mesomorphic.

Processes for the preparation of the thermotropically mesomorphic polymers described above are conventional and are described in the literature, in particular in the individual patent applications mentioned with the products.

The implant materials according to the invention contain as component B) 5 to 70, preferably 10 to 65, and in particular 25 to 60, % by weight, based on the total weight, of an apatite.

Apatite is represented by the formula $$Ca_{10}(PO_4)_6(OH,F,Cl)_2$$

and it is additionally possible for 1 to 10% by weight of carbonate ions ($CO_3^{2-}$) to be present.

The preferred component B) is hydroxyapatite $$Ca_{10}(PO_4)_6(OH)_2$$

which is commercially available. The apatite B) can contain a certain amount of whitlockite ($Ca_3(PO_4)_2$) without this having adverse effects.

The apatite can be produced by, for example, the processes described by Aoki et al. in Ceramics 10 (1975) 57–66.

If the apatite is employed in the form of spherical particles, these will have a diameter $d_{50}$ (number average) of from 0.05 to 100 μm, preferably of from 0.1 to 50 μm.

Besides components A) and B), the implant materials according to the invention can contain as component C) up to 60, preferably 0.5 to 50, and in particular 2 to 40, % by weight of other fillers different from B).

Examples which may be mentioned in this connection are kaolin, terracotta, talc, mica, calcium silicate, feldspar, sillimanite, bentonite, glass flakes, glass powder (powdered quartz), glass beads, calcium carbonate, barium carbonate, magnesium carbonate, dolomite, barium sulfate, calcium sulfate, aluminum oxide, antimony trioxide, magnesium oxide, titanium dioxide, zinc oxide, quartz, flint glass and diatomaceous earth.

It is obvious that in the case of physiologically objectionable or toxic fillers care must be taken that the filler does not come into contact with the organic tissue; biologically compatible fillers are generally preferred.

It is also possible to employ fibrous fillers as component C) to increase the rigidity further. Only metal fibers, carbon fibers and glass fibers of the various commercial types will be mentioned here. Others which can be used are inorganic fibers made from rock wool, zirconium oxide, mixed aluminum/silicon oxides, potassium titanate, barium titanate, silicon carbide and aluminum oxide. All these products are commercially available. Other possible fibrous fillers are to be found in EP-A 206,600.

Particular mention should also be made of glass fibers which have a substantial calcium phosphate content. Particularly suitable in this connection are glass fibers which have a total CaO and $P_2O_5$ content of not less than 15% by weight, with the Ca/P molar ratio being in the range from 0.3:1 to 4.0:1, preferably from 0.8:1 to 2.0:1.

Also suitable are glass fibers coated with calcium phosphate compounds of this type.

Fibrous fillers of the two latter types, as well as processes for the preparation thereof, are described in DE-A 3,542,535.

The simplest way of producing the implant materials according to the invention is to mix the apatite B) and, where appropriate, the other fillers C) into a melt of the thermotropically mesomorphic polymer A). This can be carried out most simply in an extruder or an appropriate mixing device conventional for this purpose.

After the mixture has been produced it is possible to produce implant materials in almost any desired shape by injection molding, ie. the production is considerably simpler than with previously disclosed implants based on metals or ceramic materials, the shaping of which entails considerable expense.

The implant materials according to the invention are very compatible with the intact tissue in the immediate vicinity of the site of implantation and, at the same time, have great rigidity and strength. In particular, it is possible to adjust the rigidity of the implant to that of bone so that no substantial Young's modulus cracks take place at the interfaces and there is appropriate loading of the bone by the endoprosthesis. In addition, the implant materials according to the invention have great resistance to radiation, which means that they can be efficiently sterilized by $\gamma$ rays. Moreover, as already mentioned, their production is particularly simple and low-cost.

We claim:

1. An implant material for replacing hard tissue, containing as essential components A) 30 to 95% by weight of a thermotropically mesomorphic polymer wherein said polymer comprises at least one aromatic monomer unit, B) 5 to 70% by weight of an apatite and C) 0 to 60% by weight of a fibrous or particulate filler which differs from B).

2. An implant material as claimed in claim 1, wherein the thermotropically mesomorphic polymer is a polycondensate from the group consisting of polyesters, polyesters amides, polyester imides, polyester carbonates, polyether esters, polyether ester amides, polyester amide imides, polyester carbamides and polyether ester imides.

3. An implant material as claimed in claim 1 or 2, wherein the apatite is hydroxyapatite.

4. An implant material as claimed in claim 1, wherein said thermotropically mesomorphic polymer is completely aromatic.

5. An implant material as claimed in claim 1, wherein said thermotropically mesomorphic polymer contains monomer units derived from aromatic dicarboxylic acids.

6. An implant material as claimed in claim 1, wherein said thermotropically mesomorphic polymer contains monomer units derived from aromatic diols, aromatic diamines, aromatic diols substituted with an amino or hydroxyl group, or aromatic diamines substituted with an amino or hydroxyl group.

7. An implant material as claimed in claim 1, wherein said thermotropically mesomorphic polymer contains monomer units derived from aromatic hydroxycarboxylic acids or aromatic aminocarboxylic acids.

8. An implant material as claimed in claim 1, wherein said thermotropically mesomorphic polymer contains monomer units derived from aromatic thiocarboxylic acids, aromatic dithiols or thiophenols.

9. An implant material as claimed in claim 1, wherein said thermotropically mesomorphic polymer contains monomer units derived from aliphatic dicarboxylic acids.

10. An implant material as claimed in claim 1, wherein said thermotropically mesomorphic polymer contains monomer units derived from aliphatic diols, aliphatic diamines, aliphatic diols substituted with an amino or hydroxyl group or aliphatic diamines substituted with an amino or hydroxyl group.

11. An implant material as claimed in claim 1, wherein said thermotropically mesomorphic polymer contains monomer units derived from cis-1,4-cyclohexane dicarboxylic acid, trans-1,4-cyclohexane dicarboxylic acid or 1,3-cyclohexane dicarboxylic acid.

* * * * *